United States Patent [19]

Limjuco et al.

[11] 4,220,584
[45] Sep. 2, 1980

[54] E. COLI ENTEROTOXIN VACCINE FOR VETERINARY AND HUMAN USE

[75] Inventors: Guadalupe A. Limjuco, Scotch Plains; Yashwant D. Karkhanis, Fanwood; Dennis J. Carlo, South Amboy, all of N.J.

[73] Assignee: Merck & Co., Inc., Rahway, N.J.

[21] Appl. No.: 873,181

[22] Filed: Jan. 30, 1978

[51] Int. Cl.$^2$ ............ A61K 37/02; A61K 39/02
[52] U.S. Cl. ............... 260/112 R; 424/87; 424/92
[58] Field of Search .......... 260/112 R; 424/92

[56] References Cited

U.S. PATENT DOCUMENTS

| | | | |
|---|---|---|---|
| 3,483,290 | 12/1969 | Berger et al. | 424/92 |
| 4,029,762 | 6/1977 | Galanos et al. | 260/112 R X |
| 4,057,685 | 11/1977 | McIntire | 260/112 R X |

FOREIGN PATENT DOCUMENTS 768078  6/1970  France ........................ 424/92

OTHER PUBLICATIONS

Jones et al., *The Veterinary Record*, vol. 74, No. 7 (1962), 202–204.
Gill et al., *J. Inf. Dis.*, vol. 133 (Suppl.) (1976), S103–S107.
Evans et al., *J. Inf. Dis.*, vol. 133 (Suppl.) (1976), S97–S102.
Finkelstein et al., *J. Inf. Dis.*, vol. 133 (Suppl.) (1976), S120–S137.

*Primary Examiner*—Walter C. Danison
*Attorney, Agent, or Firm*—Theresa Y. Cheng; Mario A. Monaco

[57] ABSTRACT

A vaccine against *E. coli* caused diarrhea is prepared from an isolate of the homogeneous heat-labile enterotoxin of human strain MB3353 of *Escherichia coli*, ATCC 31361, or of the porcine strain MB3708, ATCC 31362. The toxin, which is a protein, is a low molecular weight species of 10,000–13,000.

2 Claims, No Drawings

E. COLI ENTEROTOXIN VACCINE FOR VETERINARY AND HUMAN USE

DISCLOSURE OF THE INVENTION:

This invention relates to a vaccine for immunization against diarrheal disease caused by enterotoxigenic *Escherichia coli*. Certain strains of *E. coli* produce an enterotoxin which is responsible for inducing diarrhea in humans and animals. This diarrhea is known as "Traveller's Diarrhea" or "Infantile Diarrhea". Two forms of this toxin are now known to exist, heat-stable (ST) and heat-labile (LT). Both toxins are controlled by extra chromosomal genetic factors and can be transferred to certain other bacteria by sexual conjugation. The diarrheagenic action of these toxins involves extensive loss of water and electrolytes, mediated through stimulation of adenylate cyclase activity, which results in the increase in the intracellular concentration of cyclic AMP.

The labile toxin (LT) form has been isolated in several laboratories [Finkelstein et al., *J. Inf. Dis.* 133 (Suppl.), S120 (1976); Dorner, *J. Biol. Chem.*, Vol. 250, No. 22, pp. 8712–8719 (1975); Dorner et al., *J. Inf. Dis.* 133 (Suppl.) S142 (1976); Dafni et al., *J. Inf. Dis.* 133 (Suppl.) S138 (1976); Evans et al., *J. Inf. Dis.* 133 (Suppl.) S97 (1976).] There is no general agreement on the purity of any of these preparations, nor has any been shown to have the immunological potential to provide protection against diarrhea induced by the toxin.

We have isolated a homogenous preparation of LT from two enterotoxinogenic *E. coli* strains. The toxin, which is a protein, is a low molecular weight species of 10,000–13,000; dansylation for N-terminal amino acid and SDS-acrylamide electrophoresis show that it is homogenous. This species is both toxic and immunogenic. The vaccine can be used in humans and animals to protect against *E. coli* infections.

Active immunication of rabbits with the purified LT induces antibodies which protect them against diarrhea induced by the same preparation; pre-incubation of antibody with the toxin also induces neutralization. A toxoid made from this preparation has been shown to be non-toxic while still retaining its original immunogenic activity. This preparation is a viable vaccine candidate against diarrhea induced by enterotoxigenic *E. coli*, or other gram-negative bacteria.

The vaccine can be prepared from a culture of *E. coli* strain MB3353 or strain MB3708. The enterotoxin is isolated from the culture filtrate. The rabbit ileal loop model is used to study the influence of the toxin on fluid secretion into the intestinal lumen.

The cultures of *E. coli* strain MB3353, ATCC 31361, or *E. coli* strain MB3708, ATCC 31362, are both deposited with the American Type Culture Collection, Rockville, MD 20852, are grown according to the following procedure.

The culture was grown on nutrient agar plates at 37° C. in a candle jar. After 20 hrs., the bacteria were resuspended and used to inoculate one liter of syncase medium (Finkelstein et al., *The Journal of Immunology*, 96 No. 1 pp. 440–449, 1966) in a two liter Erlenmeyer flask which was incubated at 37° C. on a rotary shaker at 200 rpm (New Brunswick Scientific). After 4 hrs., the optical density (O.D. at 660 nm) reached 1.6 and the culture was inoculated into a 14 liter fermentor (New Brunswick Scientific, model MA 114) containing 9 liter media. The growth conditions were 37° C., 200 rpm and 2 liter air flow/min. The O.D., read every two hrs., reached a maximum of 2.0 after 8 hrs. incubation. The culture was cooled to 20° C. and harvested into thimerosol (ethylmercurithiosalicylic acid sodium salt, Fisher Scientific) at a concentration of 1 g. per 10 liter culture fluid. The bacteria were collected in a Sharples centrifuge at 28,000 rpm.

When growing cultures from a lyophilized tube, the following procedure is preferred, which results in both preparation of slants or other lyophiles:

1. The pellet from the lyophilized tube is suspended in 1.0 ml of 0.85% saline.
2. 0.2 ml of this suspension is used to inoculate each of four slants of Nutrient Agar.
3. The growth from the four slants is suspended in 5 ml of 15% sterile skim milk solution prepared from BBL's Skim Milk Powder.
4. 0.15 ml aliquots of the suspension are placed in freeze-dry ampoules and freeze-dried.

After fermentation is terminated, the desired solids containing the protein fraction are isolated and purified, according to the following three-step procedure: $(NH_4)_2SO_4$ precipitation, chromatography on agarose 1.5 m and hydroxylapatite (HTP). The HTP chromatography gave two peaks. The first contained active toxin while the second peak, although equally active, was contaminated with other proteins. The presence of a small shoulder associated with the first peak of HTP was consistent in several chromatographies. In activity and chemical characteristics it is similar to the first peak material.

The purified toxin contained 90% protein, 2% hexose and does not have 2-Keto deoxy octonic acid. It gives negative limulus lysate activity, at 0.5 ng/ml (Lin et al., *Biochemica et Biophysics Acta* 261, pp. 284–289, 1972.)

The molecular weight of the enterotoxin is about 10,000. It is a single chain protein. It is determined by
(a) gel filtration method using
  (1) Sephadex G-100 column equilibrated with 0.02 M TRIS-HCl pH 7.2.
  (2) Another Sephadex G-100 column (exactly same size and bed volume as above) was equilibrated with 8 M urea in 0.02 M TRIS-HCl pH 7.2. [A calibration curve for a given set of proteins was prepared which defines the relationship between the elution volumes of a set of proteins and the logarithm of their respected molecular weights. A $K_{AVE}$ for each protein is calculated and plotted against the logarithm of its molecular weight on semi-logarithm paper. The $K_{AVE}$ for the unknown is calculated and its molecular weight can be read directly from the standard curve.]
(b) by sucrose density gradient. A gradient of 5–20% sucrose was carefully layered into a cellulose nitrate tube, in such a way that the 20% solution is at the bottom and the 5% solution is at the top. Six tubes were prepared. A given set of proteins were used as markers (one protein for each tube). The markers and the enterotoxin were layered on top and the tub were spun at 40,000 rpm (280,000 g) for 24 hours. After the run, 0.2 ml fractions were withdrawn from the top of each tube and the proteins were monitored by O.D. A calibration curve was prepared by plotting the position of the protein in the gradient against the logarithm of the molecular weight on a semi-logarithm paper. The position of the enterotoxin in the gradient is determined and its molecular weight read directly from the calibration curve. The molecular weight is 10,000.

In addition to molecular weight, the N-terminal of the enterotoxin is alanine determined by the dansylation method.

A detailed description of this purification procedure follows (all steps are carried out at 4° C. unless otherwise noted).

STEP 1:

Solid $(NH_4)_2SO_4$ crystals were added to give a final concentration of 50% saturation. The solution was stirred while the salt was added until all the crystals were dissolved. After overnight standing at 4° C., the solution was centrifuged at 13,500×g for 20 minutes. The precipitate was collected and discarded, the supernatant was pooled and additional $(NH_4)_2SO_4$ crystals were added with stirring until concentration was brought to 90% saturation. After overnight standing at 4° C., the solution was centrifuged at 13,500 g for 20 minutes. The supernatant was discarded and the precipitate was collected. The precipitate was resuspended in 380 ml of 0.02 M TRIS pH 7.2 and dialyzed against 0.02 M TRIS pH 7.2 and stored for further use at −70° C. This is designated as the crude concentrate.

STEP 2:

An aliquot of the crude concentrate (40 ml.) was applied to a column (7.56 cm×50 cm) of Bio-Gel A 1.5 M 200-400 mesh, and eluted with 0.02 M TRIS pH 7.2. The filtration, with downward flow, was at a rate of 2 ml/min. Fractions (10 ml.) were collected. The column fractions were monitored by optical density reading at 280 nm (FIG. 1). Each peak was pooled, dialyzed against water and lyophilized. The heat-labile enterotoxigenic activity containing fractions were identified by the rabbit ileal loop assay.

STEP 3:

The heat-labile enterotoxigenic activity-containing fraction was further purified by adsorption chromatography on hydroxylapatite column (2.2 cm×21.5 cm) and eluted with 0.01 M $Na_2PO_4$, pH 7. Fractions (5 ml.) were collected. The column fractions were monitored by optical density reading at 280 nm (FIG. 2). A breakthrough material came out which comprised about 55% of the material applied to the column. A second peak was slightly held on the column and a linear gradient of sodium phosphate buffer pH 7.0 was applied from 0.01 to 0.2 Molar. The material was eluted out at 0.04 M sodium phosphate buffer and comprised about 19.8% of the material applied to the column. The heat-labile enterotoxigenic activity-containing fractions were identified by the rabbit ileal loop assay. The breakthrough material is the biologically active material and is homogenous by SDS gel electrophoresis criteria.

This toxin preparation is tested using the rabbit ileal loop model. The toxin was dissolved in saline prior to injection into the ileal loops of the rabbit. After 18–24 hours, rabbits were sacrificed by injecting an overdose of phentobarbital and the fluid from the dilated loop was removed. Activity was expressed as the ratio of volume of the fluid to length of the loop. For immunization, a saline solution of the toxin or toxoid was mixed with an equal volume of adjuvant and injected into rabbits at eleven day intervals; the rabbits received two injections. The initial injection was given in complete Freund's adjuvant and the subsequent one in incomplete adjuvant. One-half mg was given at each injection and the intramuscular route was used for each immunization.

The detailed description of the immunization procedure and the challenge procedure follows:

IMMUNIZATION PROCEDURE

Purified material was dissolved in PBS (phosphate buffered-saline) and mixed with equal volumes of complete Freund adjuvant (Difco) to give a final concentration of 1 mg/ml. For the first injection, each rabbit (total of 5) was given 0.5 ml. (500 μg) of the above preparation. After 10 days, the rabbits were injected with 0.5 ml. (500 μg) of a preparation made with equal volumes of toxin and incomplete Freund adjuvant. After 10 days, the rabbits were again given a 0.5 ml. (500 μg) boost with the same preparation. One week after the last injection, the rabbits were challenged. Total immunizing dose was 1.5 mg of the purified toxin.

CHALLENGE PROCEDURE

The same purified heat-labile toxin used for immunization was used to challege all the rabbits. Challenges were performed by injecting increasing quantities (5 μg, 10 μg, 50 μg, 100 μg, 250 μg, 500 μg, 750 μg and 1000 μg) of the purified preparation into ligated small intestinal loops of the immunized rabbits. Control rabbits were likewise challenged with the purified preparation in the same manner. Uninjected rabbits were used as control. The rabbits were sacrificed after 18 hours and the volume to length ratios (ml/cm) of each loop were determined.

RESULTS

The results showed that immunized rabbits completely protected against any toxic effect up to a concentration of 500 μg. Even at a 750 μg dose, the immunized rabbit showed some protection with a volume to length ratio of 1.57.

Control rabbits challenged with increasing quantities of the purified material (2 μg, 5 μg, 10 μg, 50 μg, 400 μg) gave a volume to length ratio of from 1.31, 1.64, 1.91, 2.20 and 2.20 respectively.

A detailed description of the results obtained follows, and is summarized in Tables, 1, 2, and 3.

When this toxin preparation was injected into a rabbit at a dose of 10 μg maximum dilation of the loop was obtained. The purified preparation was used both for the immunization of rabbits and toxoid production. In Table 1 neutralization of ileal loop activity is shown utilizing different dilutions of rabbit antibody. A 1:32 dilution of antibody mixed with 400 μg of toxin completely neutralizes toxin activity as compared to the control.

TABLE 1.

Antibody neutralization of ileal loop activity. For neutralization, the toxin was mixed with varying dilutions of the antibody and incubated for 30 minutes at room temperature before injection into the loop. Toxin control (400 μg), dissolved in 0.2 ml saline, was injected into the isolated loop of the rabbit and after 18 hours the activity was measured as the ratio of the volume of the fluid in the loop to its length.

| Treatment | Antibody Dilution | Ratio (ml/cm) |
|---|---|---|
| Saline | 1:4 | 0.02 ± 0.01 |

-continued

| Treatment | Antibody Dilution | Ratio (ml/cm) |
|---|---|---|
| Toxin | | 1.88 ± 0.10 |
| Serum control** | 1:4 | 0.03 ± 0.01 |
| Serum control* | 1:8 | 1.90 ± 0.20 |
| Serum** + toxin | 1:2 | 0.02 ± 0.01 |
| Serum** + toxin | 1:4 | 0.02 ± 0.01 |
| Serum** + toxin | 1:8 | 0.08 ± 0.01 |
| Serum** + toxin | 1:16 | 0.05 ± 0.01 |
| Serum** + toxin | 1:32 | 0.05 ± 0.01 |
| Serum** + toxin | 1:64 | 1.65 = 0.50 |

*Serum of control rabbit-before immunization.
**Serum of immunized rabbit.

Results consistent with those described above were found after active immunization of rabbits; rabbits actively immunized were directly challenged in their ileal loops with our purified preparation and after 18-24 hours the ratio of volume to length determined. Control rabbits received saline in adjuvant. The results described in Table 2 clearly demonstrate the protective ability of actively induced antibody; only at a 750 μg dose of toxin was any dilation of the ileal loop observed.

TABLE 2.

Active protection of rabbits** immunized with the purified heat-labile *E. coli* enterotoxin. After immunization with the enterotoxin, the rabbits were challenged with the same preparation utilizing various concentrations of toxin.

| Fraction | Amount Used (μg) | Ratio* ml/cm |
|---|---|---|
| Saline control | — | 0.02 ± 0.01 |
| Toxin | 5 | 0.02 ± 0.01 |
| Toxin | 10 | 0.02 ± 0.01 |
| Toxin | 50 | 0.02 ± 0.01 |
| Toxin | 100 | 0.02 ± 0.01 |
| Toxin | 150 | 0.02 ± 0.01 |
| Toxin | 200 | 0.02 ± 0.01 |
| Toxin | 250 | 0.06 ± 0.01 |
| Toxin | 500 | 0.06 ± 0.01 |
| Toxin | 750 | 1.57 ± 0.53 |

*Ratio of the volume of liquid to length of isolated loop. Control rabbits (3 rabbits), not immunized with the toxin, gave ratios from 1.31-2.20 when challenged with toxin at varying amounts from 2-50 μg.
**Four rabbits used in the test.

Since the toxin possessed both toxic and immunologic activity, we detoxified it by heating at 60° C. for 30 minutes; the resulting toxoid was devoid of toxic activity as determined by the ileal loop assay. Rabbits immunized with toxoid when challenged with an active LT preparation failed to show any diarrhea. The results shown in Table 3 demonstrate that the toxoid has the ability to induce protective antibody. Even with a 500 μg dose of LT, no demonstrable effect of loop dilation could be shown.

TABLE 3.

Active protection of the rabbit by the toxoid obtained by heating Lt preparation at 60° C. for 30 minutes. The rabbit was challenged with the active LT preparation from which the toxoid was obtained.

| Treatment | Amount μg | Ratio* vol. length |
|---|---|---|
| Toxoid | 5 | 0.02 ± 0.01 |
| Toxoid | 10 | 0.02 ± 0.01 |
| Toxoid | 25 | 0.02 ± 0.01 |
| Toxoid | 50 | 0.02 ± 0.01 |
| Toxoid | 100 | 0.02 ± 0.01 |
| Toxoid | 200 | 0.02 ± 0.01 |
| Toxoid | 500 | 0.02 ± 0.01 |

*A control rabbit gave a ratio of 1.61 when challenged with 500 μg of LT preparation.
**Average of 2 rabbits used.

The vaccine can be prepared from the toxin after purification and dilution with a sterile pharmaceutical liquid carrier, according to methods known in the art. The vaccine so prepared can be used in single dosage or multiple forms to give prophylactic protection against *E. coli* induced diarrhea in humans or animals. Immunity can be sustained for from a few days to 3-4 months with a single injection. The single dose level is from 25 μg to 1000 μg, and can be 25 μg to 250 μg.

In large animals such as cows, data has been collected which indicates that immunity conferred by use of the vaccine can be induced in a female and subsequently passively transferred to the progeny. This activity can also be useful in human protection, i.e, inducing immunity in adult women who pass on the immunity through placental transfer or breast feeding of their children. This data is found in the following example.

NEUTRALIZATION OF *E. COLI* ENTEROTOXIN WITH THE COLOSTRUM OF IMMUNIZED COWS

Immunization Procedure:

Three pregnant cows were immunized with LT. Two cows, No. 472 and No. 459 received two injections, 500 μg each, a total of 1.0 mg; a third cow, No. 8889, received only one injection, 500 μg.

At parturition, colostrum were taken. Control cows were given saline only.

Neutralization:

Colostrum from control cows and immunized cows were diluted with PBS (1:2 to 1:1024). Each dilution was mixed with equal volume of LT (750 μg), incubated for 30 minutes at 37° C. and injected into ligated loops of rabbits. PBS alone (negative control), LT alone, 750 μg (positive control) and colostrum alone of both control and immunized cows were injected into ligated loops of rabbits. After 18 hours, the rabbits were sacrificed and the fluid from the detailed loop was removed. Activity was expressed as the ratio of volume of the fluid to length of the loop. Results are shown in the following tables, 4, 5, and 6:

TABLE 4

NEUTRALIZATION OF E. COLI ENTEROTOXIN WITH COLOSTRUM OF IMMUNIZED COW (No. 472)

| | Amount Enterotoxin (μg) | Colostrum Dilution | Ratio Vol. Fluid/ Length |
|---|---|---|---|
| Saline control | 750 | 1:4 | 0.02 ± 0.01 |
| Colostrum control alone | — | 1:4 | 0.05 ± 0.01 |
| LT Enterotoxin alone | 750 | — | 1.80 ± 0.10 |
| LT Enterotoxin + Control colostrum | 750 | 1:4 | 1.82 ± 0.10 |
| No. 472 Colostrum alone | | 1:4 | 0.04 ± 0.01 |
| No. 472 Colostrum + LT Enterotoxin | 750 | 1:2 | 0.05 ± 0.01 |
| No. 472 Colostrum + LT Enterotoxin | 750 | 1:4 | 0.04 ± 0.01 |

TABLE 4-continued

NEUTRALIZATION OF E. COLI ENTEROTOXIN WITH COLOSTRUM OF IMMUNIZED COW (No. 472)

| | Amount Enterotoxin (μg) | Colostrum Dilution | Ratio Vol. Fluid/Length |
|---|---|---|---|
| + LT Enterotoxin No. 472 Colostrum | 750 | 1:8 | 0.05 ± 0.01 |
| + LT Enterotoxin No. 472 Colostrum | 750 | 1:16 | 0.05 ± 0.01 |
| + LT Enterotoxin No. 472 Colostrum | 750 | 1:32 | 0.05 ± 0.01 |
| + LT Enterotoxin No. 472 Colostrum | 750 | 1:64 | 0.05 ± 0.01 |
| + LT Enterotoxin No. 472 Colostrum | 750 | 1:128 | 1.20 ± 0.20 |
| + LT Enterotoxin No. 472 Colostrum | 750 | 1:256 | 1.45 ± 0.10 |
| + LT Enterotoxin No. 472 Colostrum | 750 | 1:512 | 1.80 ± 0.10 |
| + LT Enterotoxin | 750 | 1:1024 | 1.80 ± 0.10 |

TABLE 5

NEUTRALIZATION OF E. COLI ENTEROTOXIN WITH COLOSTRUM OF IMMUNIZED COW (No. 459)

| | Amount Enterotoxin (μg) | Colostrum Dilution | Ratio Vol. Fluid/Length |
|---|---|---|---|
| Saline control | — | — | 0.02 ± 0.01 |
| Colostrum Control alone | — | 1:4 | 0.05 ± 0.01 |
| LT Enterotoxin alone | 750 | — | 1.80 ± 0.10 |
| LT Enterotoxin + control colostrum | 750 | 1:4 | 1.82 ± 0.10 |
| No. 459 Colostrum alone | — | 1:4 | 0.05 ± 0.01 |
| No. 459 Colostrum + LT Enterotoxin | 750 | 1:2 | 0.03 ± 0.01 |
| No. 459 Colostrum + LT Enterotoxin | 750 | 1:4 | 0.03 ± 0.01 |
| No. 459 Colostrum + LT Enterotoxin | 750 | 1:8 | 0.04 ± 0.01 |
| No. 459 Colostrum + LT Enterotoxin | 750 | 1:16 | 0.03 ± 0.01 |
| No. 459 Colostrum + LT Enterotoxin | 750 | 1:32 | 0.04 ± 0.01 |
| No. 459 Colostrum + LT Enterotoxin | 750 | 1:64 | 1.10 ± 0.01 |
| No. 459 Colostrum + LT Enterotoxin | 750 | 1:128 | 1.45 ± 0.01 |
| + LT Enterotoxin | 750 | 1:256 | 1.20 ± 0.01 |

TABLE 6

NEUTRALIZATION OF E. COLI ENTEROTOXIN WITH COLOSTRUM OF IMMUNIZED COW (No. 8889)

| | Amount Enterotoxin (μg) | Colostrum Dilution | Ratio Vol. Fluid/Length |
|---|---|---|---|
| Saline control | — | — | 0.02 ± 0.01 |
| Colostrum control alone | — | 1:4 | 0.04 ± 0.01 |
| LT Enterotoxin alone | 750 | — | 2.20 ± 0.10 |
| LT Enterotoxin + Control Colostrum | 750 | 1:4 | 1.95 ± 0.10 |
| No. 8889 Colostrum alone | — | 1:4 | 0.03 ± 0.01 |
| No. 8889 Colostrum + LT Enterotoxin | 750 | 1:2 | 0.02 ± 0.01 |
| No. 8889 Colostrum + LT Enterotoxin | 750 | 1:4 | 0.03 ± 0.01 |
| No. 8889 Colostrum + LT Enterotoxin | 750 | 1:8 | 0.02 ± 0.01 |
| No. 8889 Colostrum + LT Enterotoxin | 750 | 1:16 | 0.02 ± 0.01 |
| No. 8889 Colostrum + LT Enterotoxin | 750 | 1:32 | 0.03 ± 0.01 |
| No. 8889 Colostrum + LT Enterotoxin | 750 | 1:64 | 0.02 ± 0.01 |
| No. 8889 Colostrum + LT Enterotoxin | 750 | 1:128 | 0.02 ± 0.01 |
| No. 8889 Colostrum + LT Enterotoxin | 750 | 1:256 | 1.35 ± 0.02 |

What is claimed is:

1. A heat-labile enterotoxin vaccine for immunization against *E. Coli* caused diarrhea which is isolated from *E. Coli* culture filtrate having a molecular weight of 10,000–13,000 when determined by gel filtration or by sucrose density gradient; containing 90% protein, 2% hexose, no 2-keto deoxy octonic acid; being a homogeneous single chain protein with N-terminal alanine when determined by the dansylation method and SDS-acrylamide electrophoresis; and showing no activity in the limulus lysate assay.

2. The process for preparing a heat-labile enterotoxin comprising:
   (a) growing a culture of *E. coli* in a suitable culture medium;
   (b) isolating the protein from the culture medium by $(NH_4)_2SO_4$ precipitation to form a crude concentrate;
   (c) chromatographing the crude concentrate solution of protein on agarose; and eluting with a suitable buffer such as 0.02 M TRIS pH 7.2, ammonium bicarbonate pH 7.2, or ammonium acetate pH 7.2.
   then (d) chromatographing the resulting solution on hydroxylapatite and eluting with 0.01 M sodium phosphate pH 7.0;
   recovering the purified product thereby produced.

* * * * *